US006177266B1

(12) United States Patent
Krishnamurthy et al.

(10) Patent No.: US 6,177,266 B1
(45) Date of Patent: *Jan. 23, 2001

(54) RAPID IDENTIFICATION OF BACTERIA BY MASS SPECTROMETRY

(75) Inventors: Thaiyalnayaki Krishnamurthy, Ellicott City; Philip L. Ross, Jessup, both of MD (US)

(73) Assignee: The United States of America as represented by the Secretary of the Army, Washington, DC (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/245,666

(22) Filed: Feb. 8, 1999

Related U.S. Application Data

(63) Continuation of application No. 08/847,419, filed on Apr. 24, 1997, now abandoned.
(60) Provisional application No. 60/016,438, filed on Apr. 29, 1996.

(51) Int. Cl.$^7$ .................................................. C12N 13/00
(52) U.S. Cl. .................................... 435/173.1; 435/173.4; 436/173; 436/518; 250/281; 250/282; 250/287; 313/564
(58) Field of Search .................................. 436/518, 173; 250/281, 282, 287; 435/173.1, 173.4; 313/564

(56) References Cited

PUBLICATIONS

Krishnamurthy et al: "Detection of Pathogenic and Non–Pathogenic Bacteria by Matrix–assisted Laser Desorption/Ionization Time–of–Flight Mass Spectrometry". Rapid Communications in Mass Spectrometry vol. 10, 883–88 (1996).

Krsihnamurthy et al: "Rapid Indentification of Bacteria by Direct Matric–assisted Laser Desorption/Ionization Mass Spectrometric Analysis of Whole Cells", Rapid Communications in Mass Spectrometry vol. 10, 1992–1996 (Dec. 1996).

Krsihnamurthy et al; "Bacterial Detection by Mass Spectrometry". Indian Society for Mass Spectrometry pp. 105–122 (Nov. 1996).

Zaluzec et al; "Matrix–Assisted Laser Desorption Ionization Mass Spectrometry Applications in Peptide and Protein Characterization". Protein Expression and Purification vol. 6, pp. 109–123 (1995).

Holland et al; Rapid Indentification of Intact Whole Bacteria Based on Spectral patterns using Matrix–assisted Laser Desorption/Ionization with Time–of–Flight Mass Spectrometry. Rapid Communications in Mass Spectrometry vol. 10, 1227–1232 (Jul. 1996).

Cain et al; Differentiation of Bacteria Using Protein Profiles from Matrix–assisted Laser Desorption/Ionization with Time–of–Flight Mass Spectrometry. Rapid Communications in Mass Spectrometry vol. 8, 1026–1030 (1994).

Harvey; "Matrix–assisted Laser Desorption/Ionization Mass Spectrometry of Oligosaccharides and glycoconjugates". Journal of Chromatography a 720 (1996) pp. 429–446.

Chevrier et al. Matrix–assisted Laser Desorption/Ionization with Time–of–Flight Mass Spectrometry Based on a 600 ps. 1.2mJ Nitrogen Laser. Rapid Communications in Mass Spectrometry vol. 5, 611–617 (1991).

DRDE, Gwalior; "Proceedings of Seventh National Symposium on Mass Spectrometry". Indian Society for Mass Spectrometry (ISMAS) Mumbai, India (1996).

Claydon et al.; "The Rapid identification of intact microorganisms using mass spectrometry". Nature Biotechnology vol. 14, pp. 1584–1586, Nov. 1996.

Liang et al.; Determination of Bacterial Protein Profiles by Matrix–assisted Laser Desorption/Ionization Mass Spectrometry with High–performance Liquid Chromatography. Rapid Communication in Mass Spectrometry, vol. 10, pp. 1219–1226 (1996).

*Primary Examiner*—Jennifer Graser
(74) *Attorney, Agent, or Firm*—Ulysses John Biffoni; Vincent J. Ranucci

(57) ABSTRACT

A method for the identification of bacteria using genus, species and strain specific biomarkers. The biomarkers are generated by matrix assisted laser desorption ionization time-of-flight mass spectrometry (MALDI-TOF-MS) analysis of either cellular protein extracts or whole cells. Biomarkers for a number of pathogenic bacteria are disclosed.

13 Claims, No Drawings

RAPID IDENTIFICATION OF BACTERIA BY MASS SPECTROMETRY

This application is a continuation of application Ser. No. 08/847,419, filed on Apr. 24, 1997, now abandoned, which in turn is a nonprovisional continuation of provisional application Ser. No. 60/016,438, filed on Apr. 29, 1996.

GOVERNMENTAL INTEREST

The invention described herein may be manufactured, used and licensed by or for the U.S. Government.

FIELD OF THE INVENTION

The present invention relates generally to the rapid identification of bacteria in environmental and biological samples. More specifically, the present invention relates to a method for the chemotaxonomic classification of bacteria with genus, species and strain specific biomarkers generated by matrix assisted laser desorption ionization time-of-flight mass spectrometry (MALDI-TOF-MS) analysis of either cellular protein extracts or whole cells.

BACKGROUND OF THE INVENTION

Rapid and accurate microbial identification is critical in diagnosing diseases, predicting on-coming public health hazards, monitoring potential contamination in stored foods and grains, regulating bioprocessing operations and recognizing warfare threats. It is important not only to rapidly distinguish between related organisms but also to unambiguously identify species and strains in complex matrices for risk assessment in field situations.

The classification of micro-organisms has traditionally been based on biochemical and morphological culturing tests. Recently, several instrumental analytical techniques have been developed which enhance the speed and accuracy of identification of bacteria cells. In these techniques, the biochemical components of bacteria cells are examined to determine chemotaxonomic markers which are specific for each bacteria species. The chemotaxonomic markers, or biomarkers, may be any one or a combination of the classes of molecules present in the cells such as lipids, phospholipids, lipopolysaccharides, oligosaccharides, proteins and DNA.

For example, a commercial microbial identification system uses gas chromatographic analysis of fatty acid methyl esters (Microbial Identification, Inc., Newark, Del.). Chemotaxonomic identification of bacteria based on fatty acid or whole-cell pyrolysis mass spectra and fast-atom bombardment mass spectrometric analysis of phospholipids has also been reported. These techniques analyze primarily the lower molecular weight lipids of the cell.

Bacteria may also be differentiated on the basis of cellular protein content. Since the proteins found in bacteria provide indirect genetic information on the organism and are related to bacterial virulence, protein content is specific to individual strains. The most established technique for examining cellular protein content is sodium deodecyl sulfate-polyacrylamide gel electrophoresis (SDS-PAGE) which produces characteristic migration patterns for different bacteria species. Identification of a bacteria producing a particular migration pattern is accomplished by computerized comparison with reference gel patterns. However, because SDS-PAGE analysis is slow, labor intensive and requires fairly large amounts of sample material, it is not particularly useful for rapid identification of bacteria, particularly in field situations.

A limited number of recent reports have investigated the applicability of various mass spectrometric techniques for generating bacteria specific protein profiles. These techniques generally employ electrospray ionization (ESI) or matrix-assisted laser desorption ionization (MALDI) of bacteria protein extracts followed by mass spectrometric (MS) or tandem mass spectrometric (MS/MS) analysis. For example, the MALDI technique, combined with time-of-flight mass spectrometry (TOF-MS), has been used to differentiate bacteria using a crude protein extract requiring minimal sample preparation. (See T. C. Cain, D. M. Lubman, and W. J. Weber, Jr., *Rapid Commun. Mass Spectrom.*, Vol. 8, pp. 1026–1030 (1994)). In addition, two different groups have reported the identification of intact bacteria with MALDI-TOF-MS. (See R. D. Holland et al., *Rapid Communications in Mass Spectrometry*, Vol. 10, pp. 1227–1232 (1996) and M. A. Claydon et al., *Nature Biotechnology*, Vol. 14, pp. 1584–1586).

The MALDI-MS technique is based on the discovery in the late 1980s that desorption/ionization of large, nonvolatile molecules such as proteins can be effected when a sample of such molecules is irradiated after being codeposited with a large molar excess of an energy-absorbing "matrix" material, even though the molecule does not strongly absorb at the wavelength of the laser radiation. The abrupt energy absorption initiates a phase change in a microvolume of the absorbing sample from a solid to a gas while also inducing ionization of the sample molecules.

Detailed descriptions of the MALDI-TOF-MS technique and its applications may be found in review articles by E. J. Zaluzec et al. (*Protein Expression and Purification*, Vol. 6, pp. 109–123 (1995)) and D. J. Harvey (*Journal of Chromatography A*, Vol. 720, pp. 429–4446 (1996)), each of which is incorporated herein by reference. In brief, the matrix and analyte are mixed to produce a solution with a matrix:analyte molar ratio of approximately 10,000:1. A small volume of this solution, typically 0.5–2 $\mu l$, is applied to a stainless steel probe tip and allowed to dry. During the drying process the matrix codeposits from solution with the analyte.

Ionization of the analyte is effected by pulsed laser radiation focused onto the probe tip which is located in a short (~5 cm) source region containing an electric field. The ions formed at the probe tip are accelerated by the electric field toward a detector through a flight tube, which is a long (~1 m) field free drift region. Since all ions receive the same amount of energy, the time required for ions to travel the length of the flight tube is dependent on their mass. Thus, low-mass ions have a shorter time of flight (TOF) than heavier ions. All the ions that reach the detector as the result of a single laser pulse produce a transient TOF signal. Typically, ten to several hundred transient TOF mass spectra are averaged to improve ion counting statistics.

The mass of an unknown analyte is determined by comparing its experimentally determined TOF to TOF signals obtained with ions of known mass. The MALDI-TOF-MS technique is capable of determining the mass of proteins of between 1 and 40 kDa with a typical accuracy of ±0.1%, and a somewhat lower accuracy for proteins of molecular mass above 40 kDa.

SUMMARY OF THE INVENTION

It is an object of the present invention to provide an improved mass spectrometric method for identifying bacteria at the genus, species and strain levels.

Another object of the present invention is to provide such a method which may be applied to whole bacteria cells in the laboratory or in field situations.

Yet another object of the present invention is to provide a library of genus, species and strain specific biomarkers for use in bacteria identification by mass spectrometry.

DETAILED DESCRIPTION OF THE INVENTION

These and other objects are satisfied by the present invention which includes a method for generating unique mass spectral profiles, as well as individual biomarkers, of the proteinaceous material in bacteria extracts or whole bacteria cells by MALDI-TOF-MS, and the specific biomarkers produced by the method. The method has been described in detail elsewhere. See T. Krishnamurthy, et al., *Rapid Communications in Mass Spectrometry*, Vol 10, pp. 883–888 (1996). T. Krishnamurthy and P. Ross, *Rapid Communications in Mass Spectrometry*, Vol 10, pp. 1992–96 (1996), and T. Krishnamurthy and P. Ross, *Proceedings of Seventh National Symposium on Mass Spectrometry*, Indian Society for Mass Spectrometry, pp. 105–122 (November 1996), each of which is incorporated herein by reference.

A sample mixture is prepared by mixing a matrix solution with an unknown bacteria sample which comprises a protein extract or whole cells. A small aliquot 1 $\mu$l of the sample mixture is subjected to MS analysis in a MALDI-TOF instrument equipped with a nitrogen laser. Mass spectra are averaged over 100–200 individual laser shots, collected, and compared to MALDI-TOF-MS spectra of protein extracts or whole cells of known bacteria to identify the unknown bacteria sample.

As stated above, the present invention provides a method for generating unique mass spectral profiles for bacteria protein extracts or whole bacteria cells. These profiles contain proteinaceous biomarkers which distinguish between bacteria of different genera, species and strains. Comparable profiles are generated when the method is performed using different MALDI-TOF instruments from different manufactures. The invention will be further explained by reference to the nonlimiting examples set forth below.

EXAMPLE 1

Sample Preparation for MS Analysis

Bacteria

A number of pathogenic and nonpathogenic bacteria of different genera, species and strains were analyzed. The pathogenic bacteria strains were supplied as γ-irradiated and lyophilized samples by the U.S. Army Laboratories at Dugway Proving Ground, Utah. Nonpathogenic bacteria cells of different strains were grown in-house by incubating for 24 hrs. at 37° C. on trypticase soy agar or nutrient agar plates, harvested and lyophilized Cell lysis Lyophilized bacteria cells (1–2 mg) were suspended in 50 $\mu$l of a solution containing 10 mM Tris-HCl (pH 8.0), 0.1% sodium dodecyl sulfate (SDS), and 0.1 mM β-mercaptoethanol (BME). Alternatively, the same quantity of lyophilized bacterial cells were suspended in 50 $\mu$l of 10 mM Tris-HCl (pH 8.0), the suspended cells were sonicated using an ultramicro cell disruptor tip for 5 minutes, and then SDS and BME solutions were added to final concentrations of 0.1% and 0.1 mM, respectively.

The resulting cell solution, non-sonicated or sonicated, was incubated at 95° C. for 10 minutes, cooled, diluted with 50 $\mu$l of deionized water, and treated with 10 $\mu$l of a DNAase 1 solution (1 mg/ml). The reaction mixture was incubated at ambient temperature for 10 minutes and centrifuged. Spectrograde methanol (1 ml) was added to the supernatant liquid and the resulting solution was incubated at room temperature for 10 min. The solution was then centrifuged for 10 min. and the supernatant liquid decanted and discarded. The precipitate was air dried for 5–7 min and resuspended in 50–100 $\mu$l of a mixture of equal volumes of 100 mM ammonium bicarbonate and 1 mM calcium chloride. The resulting bacteria protein extracts were either used immediately for mass spectral analysis or were stored at −20° C. prior to use.

EXAMPLE 2

MALDI-TOF-MS Analysis

Matrix solutions contained about 10 mg/ml of either 4-hydroxy-α-cyano-cinnamic acid (4 CHCA; 10 mg/ml) or 3,5-dimethoxy-4-hydroxy cinnamic acid (sinapinic acid) in an aqueous solvent solution comprising 0.1% aqueous trifluoroacetic acid (TFA) and acetonitrile in a ratio of 70/30 (v/v).

Sample mixtures were prepared as follows. For analysis of bacterial protein extracts, 1 $\mu$l of a protein extract prepared as described in Example 1 was mixed with 9 $\mu$l of matrix solution. For analysis of whole cells, a small quantity (0.1–0.2 mg) of intact, whole cells are suspended were added to 20 $\mu$l of aqueous buffer, typically 0.1% trifluoroacetic acid, vortexed for 30 seconds, and 1 $\mu$l of the resulting suspension was either frozen for later use and thawed and combined with 9 $\mu$l of a matrix solution or used immediately.

The sample mixture, containing protein extract or whole cells, was vortexed for about 30 seconds and a 1 $\mu$l aliquot was then deposited onto the stainless steel autosampler pins of a Vestec 2000 MALDI-TOF-MS instrument (Vestec Instruments, Houston, Tex.) and allowed to air dry. The dried sample was irradiated at 337 nm from a nitrogen laser with the mass spectrometer operating in linear mode (reflection mode not operational). All experiments were conducted with the instrument operating at 26 kV acceleration voltage in linear mode, which gives an ion flight path of 1.25 meters. The instrument was also equipped with a low mass ion gate which substantially improves the sensitivity of the instrument to higher mass ions by rejecting ions below 1500 Daltons.

Mass spectra obtained during 100–200 individual laser shots, at a laser intensity approximately 10–30% above the threshold for ion appearance, were averaged and collected. The mass spectra were externally calibrated using calibrant mixtures comprising 1 pmol each of cytochrome c (12360.5 Da) or bovine insulin (5733.5 Da). Separate calibration files were generated for each sample carousel and for different days. Comparable data is achieved with internal calibration, when the concentration of the internal standard in the sample does not exceed 0.5 pmole/$\mu$l.

The mass spectra of protein extracts from mechanically and chemically lysed bacteria were found to be very similar for a particular bacterial strain. Ions of lower molecular weight were generally present in greater quantities, and thus more easily detected, in the extracts from sonicated bacteria, particularly when the bacterial sample was a gram-positive bacteria.

It was also observed that low ionization occurred when too much bacterial or protein extract was present in the sample. Thus, it is preferable to determine the optimal ratio of matrix to protein extract or whole cells for each bacteria sample. This may be done by serially diluting the protein extract or whole cell suspension in 0.1% TFA and mixing 1 μl of each dilution with 9 μl of matrix solution.

By comparing the mass spectra of samples from a number of bacteria, ions that are specific to the genus, species and/or strain of these bacteria were identified. Repeated experiments demonstrated that the measured mass/charge ratio (m/z) for a particular ion obtained with a protein extract or whole cell suspension varies slightly from experiment to experiment, within a range of 0.1%. This variation is due to the limitations observed in the mass assignments during MALDI-TOF-MS analysis. The average of the m/z ratios for that ion measured in 4–5 assays is the biomarker that was assigned to that bacteria. Any m/z measurement falling within ±0.1% of this biomarker is considered to be a genus, species or strain biomarker for that bacteria.

Mass spectral analysis of protein extracts according to the above described process consistently produced genus, species and strain specific biomarkers as shown in Table 1 below.

TABLE 1

Biomarkers for Bacteria Protein Extracts

| Organism | Genus Biomarkers (m/z) | Species Biomarkers (m/z) | Strain Biomarkers (m/z) |
|---|---|---|---|
| *Bacillus anthracis*, vollum | 6680, 6837 | 2385, 3991, 4313 | 4505 |
| *Bacillus anthracis*, sterne | 6680, 6837 | 2385, 3991, 4313 | 2789 |
| *Bacillus anthracis*, zimbabwe | 6680, 6837 | 2385, 3991, 4313 | 2850 |
| *Bacillus thuringiensis*, 4A1 | 6680, 6837 | 3932 | 5916 |
| *Bacillus thuringiensis*, 4A2 | 6680, 6837 | 3932 | 4871, 7845 |
| *Bacillus thuringiensis*, 4L2 | 6680, 6837 | 3932 | 2864, 4074, 4548, 5781 |
| *Bacillus cereus*, 6E1 | 6680, 6837 | 5269, 5537, 7365, 9533 | N/A |
| *Bacillus subtilis*, 3A1 | 6680[a] | 3757, 3871, 6304, 9146 | N/A |
| *Brucella melitensis*, melitensis wild | 7379, 8031, 9060 | N/A | N/A |
| *Brucella melitensis*, REV-1 vaccine | 7354, 8030, 9071 | N/A | N/A |
| *Brucella melitensis*, Suis wild | 7378, 8020, 9080 | N/A | 5844 |
| *Brucella melitensis*, abortus wild | 7379, 8020, 9088 | N/A | N/A |
| *Yersinia pestis*, India | 2460, 3223, 3297, 4361, 4437 | N/A | 7335 |
| *Yersinia pestis*, La Paz | 3223, 3297, 4361, 4437 | N/A | N/A |
| *Yersinia pestis*, Nairobi | 2453, 3223, 3297, 4361, 4437 | N/A | 5196, 5638, 7599, 9637 |
| *Francisella tularensis*, type B | 2622, 2770, 3205, 3274, 4120, 4747 | N/A | N/A |

[a]Doubly charged ion, corrected mass/charge ratio
N/A - Data not available

The data in Table 1 include biomarkers which distinguish between four species of Bacillus. *B. cereus* and *B. thuringiensis* have distinct species specific biomarkers at m/z 9533 and 9652, respectively. Similarly, the ion observed at m/z 4313 appears to be specific for *B. anthracis.*

Different strains of a bacteria species can also be distinguished by MALDI-TOF-MS analysis of protein extracts according to the invention. As shown in Table 1, biomarkers specific for representative strains of *B. anthracis* and *B. thuringiensis* were identified.

Similarly, mass spectral analysis of intact, whole cells by the above procedure also produced biomarkers which distinguished between bacteria at the genus, species and strain levels. Data for several bacteria strains are listed below in Table 2:

TABLE 2

Biomarkers for Whole Bacteria Cells

| Organism | Genus Biomarkers (m/z) | Species Biomarkers (m/z) | Strain Biomarkers (m/z) |
|---|---|---|---|
| *Bacillus anthracis*, zimbabwe | 4339, 5178, 6436, 6686, 7377, 9640 | 5422, 7780, 9982 | 2880 |
| *Bacillus thuringiensis*, 4D5 | 4335, 5174, 6440, 7378, 9640 | 3253, 5353 | |
| *Bacillus cereus*, 6E1 | 4334, 5165, 6437, 6680, 9640 | 3015, 4816 | |
| *Bacillus subtilis*, YB 886 | 4340 | 6913, 9130 | |
| *Brucella melitensis*, REV-1 vaccine | 7403, 9087, 16100 | 2700, 10287 | |
| *Brucella melitensis*, Abortus 2308 | 7402, 9083, 16082 | 10280 | 4512, 7664 |
| *Yersinia pestis*, 195P India | 5946, 7288, 9167, 10881 | | |
| *Francisella tularensis*, type B | 4725, 6725, 9447, 10280 | | |

Blank boxes mean Not tested.

The above data demonstrate that MALDI-TOF-MS analysis of whole cells is capable of distinguishing between virulent and nonvirulent strains of bacteria. For example, REV-1 strain of *Brucella melitensis* is a non-pathogenic strain which is commonly used as a vaccine for humans and livestock, whereas the Abortus strain of *B. melitensis* is very pathogenic. The similar ionic profiles observed during analysis of whole cells from these two strains are easily distinguished by the presence of ions at m/z 4512 and 7664 in the Abortus strain which are lacking in the REV-1 strain.

Comparison of the biomarkers generated from protein extracts and whole cells showed a number of biomarkers in common and additional, unique biomarkers for the intact cells. The data for a number of representative bacteria strains are shown in Table 3 below:

TABLE 3

Comparison of Biomarkers for Protein Extracts and Whole Cells

| Organism | Common Biomarkers (m/z) | Unique whole cell biomarkers (m/z) |
|---|---|---|
| *Bacillus anthracis*, Sterne | 4340, 6684, 6832 | 2580, 5171, 6431, 7374, 7772, 9640, 9981 |
| *Bacillus anthracis*, Zimbabwe | 4342, 6685, 6828 | 2880, 5178, 6436, 7377, 7780, 9988 |
| *Bacillus anthracis*, Vollum | 4339, 6683, 6837 | 2580, 5172, 6428, 7379, 7780, 9988 |
| *Bacillus cereus*, 6E1 | 2470, 6682, 6827 | 3015, 4816, 5174, 6437, 9634 |
| *Bacillus thuringiensis*, 4D5 | 4335, 6685 | 5174, 6440, 7378, 9640 |
| *Bacillus subtilis*, | 3898, 9130 | 4340, 6913 |
| *Brucella melitensis*, REV-1 | 6650, 7044, 7341, 9071 | 2700, 7403, 9087, 10287, 16100 |
| *Yersinia pestis*, 195P India | N/F | 5946, 7288, 9167, 10881 |
| *Francisella tularensis*, | N/F | 4725, 6725, 9447, 10280 |

N/F - none found

EXAMPLE 3

Effect of Growth Conditions on Biomarkers Generated by MALDI-TOF-MS

The potential use of pathogenic bacteria by terrorists or by a country at war is a major international concern. Thus, it would be very useful if the source of any release could be identified. Intelligence information indicates that various countries, terrorist organizations, etc. may culture pathogenic bacteria under particular growing conditions. The present invention is capable of distinguishing between the same strain of bacteria grown under different conditions.

For example, mass spectra of whole *Francisella tularensis* cells grown in four different media (ISOVitalex Agar, BCYE Agar, Mueller-Hinton Broth, and Mueller-Hinton Agar) were very similar to each other and the identification of the strain could be determined using previously assigned biomarkers (data not shown). However, comparison of the spectra showed the presence of distinct ions (see Fig 10 of T. Krishnamurthy and P. Ross, *Proceedings of Seventh National Symposium on Mass Spectrometry*, Indian Society for Mass Spectrometry, pp. 105–122 (November 1996) for each growth medium.

Similarly, MALDI-TOF-MS analysis of whole cells according to the invention is capable of identifying a bacterium regardless of whether it is in a vegetative or sporulated form. These form-specific biomarkers can be applied for determining the growth conditions which may help identify the source of a bacteria sample collected from a release site.

For practical utility, mass spectral analysis of bacteria samples should be robust, i.e., not affected by various contaminants that may be present in the sample. This need is met by the present invention.

For example, the biomarkers generated by MALDI-TOF-MS of whole cells according to the present invention are not significantly affected by the pH 3–9 of the buffer used for bacteria suspensions.

In addition, unknown bacteria samples mixed with soil have been identified using previously assigned biomarkers.

EXAMPLE 4

Analysis of a Pathogenic Bacteria Mixture

Whole bacteria cells of four pathogenic bacteria, *Bacillus anthracis, Yersinia pestis, Francisella tularensis*, and *Brucella melitensis*, were mixed in various possible combinations and subjected to MALDI-MS-TOF analysis according to the method followed in Example 2. The mass spectra obtained with each mixture (data not shown) were compared with predetermined biomarkers for these organisms. The results demonstrated that each pathogen could be detected and identified in the presence of any of the either three pathogens. Moreover, analysis of a mixture of all four pathogens showed that the each of the four bacteria in the mixture could be detected and distinguished based on the observed biomarkers in the MALDI-MS spectrum of the mixture.

While the foregoing invention has been described in detail by way of illustration and example for purposes of understanding, it will be obvious that certain changes and modifications may be practiced within the scope of the appended claims.

We claim:

1. A method for generating biomarkers specific for a known genus, species, or strain of bacteria comprising:

(a) mixing a bacteria sample comprising a suspension of whole cells of known genus, species or strain with a matrix solution to generate a sample mixture;

(b) placing an aliquot of said sample mixture on the probe tip of a time-of-flight mass spectrometer and allowing it to dry;

(c) irradiating the dried aliquot with a nitrogen laser to form ionized biopolymers;

(d) accelerating the ionized biopolymers by an electric field toward a detector through the flight tube of the time-of-flight mass spectrometer to obtain a mass spectra;

(e) averaging the mass spectra resulting from 100 to 200 laser pulses;

(f) repeating steps (a)–(e) with at least one other, non-identical bacteria sample comprising a suspension of whole cells of the same genus, species or strain;

(g) comparing the averaged mass spectra obtained for each bacteria sample;

(h) identifying at least one ion that is common to each bacteria sample; and (i) assigning an m/z measurement of the ion as a genus, species, or strain specific biomarker.

2. The method of claim 1, wherein the matrix solution comprises about 10 mg/ml of compounds selected from the group consisting of 4-hydroxy-α-cyano-cinnamic acid and 3,5-dimethoxy-4-hydroxy cinnamic acid in an aqueous solvent solution.

3. The method of claim 2, wherein the aqueous solvent solution for making matrix solutions comprises 0.1% aqueous trifluoroacetic acid (TFA) and acetonitrile in a ratio of 70/30 (v/v).

4. The method of claim 1, wherein the sample mixture comprises 1 μl of the bacteria sample and 9 μl of the matrix solution.

5. The method of claim 1, wherein the time-of-flight mass spectrometer is operated at 26 kV acceleration voltage in linear mode.

6. The method of claim 1, wherein the time-of-flight mass spectrometer is equipped with a low mass ion gate which rejects ions below 1500 Daltons.

7. A method for determining the genus, species and/or strain of an unknown bacteria sample which comprises:

(a) generating an averaged mass spectra according to steps (a)–(e) of claim 1; and (b) comparing the averaged mass spectra of the unknown bacteria sample to a plurality of genus, species or strain specific biomarkers, said biomarkers being generated according to claim 1.

8. The method of claim 7, wherein the matrix solution comprises about 10 mg/ml of compounds selected from the group consisting of 4-hydroxy-α-cyano-cinnamic acid and 3,5-dimethoxy-4-hydroxy cinnamic acid in an aqueous solvent solution.

9. The method of claim 8, wherein the aqueous solvent solution comprises 0.1% aqueous trifluoroacetic acid (TFA) and acetonitrile in a ratio of 70/30 (v/v).

10. The method of claim 7, wherein the sample mixture comprises 1 μl of the bacteria sample and 9 μl of the matrix solution.

11. The method of claim 7, wherein the time-of-flight mass spectrometer is operated at 26 kV acceleration voltage in linear mode.

12. The method of claim 7, wherein the time-of-flight mass spectrometer is equipped with a low mass ion gate which rejects ions below 1500 Daltons.

13. A biomarker library for identifying the genus, species and/or strain of an unknown bacteria sample, the library comprising genus, species or strain specific biomarkers for known bacteria generated by the method of claim 1 using bacteria selected from the group consisting of: *Bacillus anthracis, Bacillus thuringiensis, Bacillus cereus, Bacillus subtilis, Yersinia pestis, Francisella tularnsis*, and *Bucella melitensis*.

* * * * *